(12) United States Patent
Russell et al.

(10) Patent No.: US 8,137,718 B2
(45) Date of Patent: Mar. 20, 2012

(54) PROBIOTIC INFANT PRODUCTS

(75) Inventors: William Michael Russell, Evansville, IN (US); Michael Ceddia, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 491 days.

(21) Appl. No.: 12/284,230

(22) Filed: Sep. 19, 2008

(65) Prior Publication Data

US 2010/0074871 A1 Mar. 25, 2010

(51) Int. Cl.
| | |
|---|---|
| A23C 9/12 | (2006.01) |
| A23D 7/00 | (2006.01) |
| A01N 63/00 | (2006.01) |
| A61K 38/43 | (2006.01) |
| C12P 7/64 | (2006.01) |

(52) U.S. Cl. ....... 426/61; 424/93.1; 424/93.3; 424/93.4; 426/601; 435/134

(58) Field of Classification Search .................. None
See application file for complete search history.

(56) References Cited

U.S. PATENT DOCUMENTS

| | | | |
|---|---|---|---|
| 5,843,698 | A | 12/1998 | Sorensen |
| 5,922,375 | A | 7/1999 | Luchansky et al. |
| 6,074,815 | A | 6/2000 | Sorensen |
| 6,150,127 | A | 11/2000 | Sorensen |
| 7,179,460 | B2 | 2/2007 | Dennin et al. |
| 2007/0031537 | A1 | 2/2007 | Secretin |
| 2008/0044481 | A1* | 2/2008 | Harel ............................ 424/490 |

FOREIGN PATENT DOCUMENTS

WO 2008117267 10/2008

OTHER PUBLICATIONS

McCracken, V.J., et al., *Probiotics and the immune system*, Probiotics a Critical Review, Tannock, GW (ed), Horizon Scientific Press, UK. 1999, p. 85-113.
Savage, D.C., *Interaction between the host and its microbes*, Microbial Ecology of the Gut, Clark and Bauchop (eds), Academic Press,London. 1977, p. 277-310.
Kagnoff, M.F., *Immunology of the intestinal tract*, Gastroenterol, 1993; 105(5): 1275-80.
Lamm, M.E., *Interaction of antigens and antibodies at mucosal surfaces*, Ann. Rev. Microbiol. 1997; 51:311-40.
Raychaudhuri, S, et al., *Fully mobilizing host defense: building better vaccines*, Nat. Biotechnol., 1998; 16:1025-31.
Stallmach, A., et al., *Induction and modulation of gastrointestinal inflammation*, Immunol. Today, 1998; 19 (10): 438-41.
De Waal Malefyt, R., et al., *Interleukin 10 (IL-10 ) and viral IL-10 strongly reduce antigen-specific human T cell proliferation by diminishing the antigen-presenting capacity of monocytes via downregulation of class II major histocompatibility complex expression*, J. Exp. Med. Oct. 1, 1991; 174(4):915-24.
Masco, L., et al., *Identification of Bifidobacterium species using rep-PCR fingerprinting*, Syst. Appl. Microbiol. Nov. 2003; 26(4):557-63. PMID: 14666984.
Tagg, Jr, et al., *Bacteriocins of Gram positive bacteria*, Bacteriol. Rev. 1976; 40:722-756.
Crabbe, PA, et al., *The normal microbial flora as a major stimulus for proliferation of plasma cells synthesizing IgA in the gut. The germ free intestinal tract*, Into. Arch. Allergy Appl. Immunol., 1968; 34:362-75.
Henderson, B., et al., *Bacteria-Cytokine interactions in health and disease*, Portland Press, 79-130.
Arai, KI, et al., *Cytokines: coordinators of immune and inflammatory responses*, Annu. Rev. Biochem. 1990; 59:783-836.
McGee, DW, et al., *A synergistic relationship between TNF-alpha, IL-1 beta, and TGF-beta 1 on IL-6 secretion by the IEC-6 intestinal epithelial cell line*, Immunology 1995, Sep; 86(1): 6-11.
Wu, S., et al., *Transfection of ovarian cancer cells with tumour necrosis factor alpha (TNF-alpha ) antisense mRNA abolishes the proliferative response to interleukin-1 (IL-1 ) but not TNF-alpha*, Bynecol. Oncol. 1994, Apr; 53(1):59-63.
Rowland, IR, *Toxicology of the colon: role of the intestinal microflora*, Gibson G.R. (ed). Human Colonic Bacteria: Role in Nutrition, Physiology and Pathology, 1995, p. 155-174. Boca Raton CRC Press.
Walker, RI, *New strategies for using mucosal vaccination to achieve more effective immunization*, Vaccine, 1994; 12: 387-400.
Steidler, L., et al., *Mucosal delivery of murine interleukin-2 (IL-2 ) and IL-6 by recombinant strains of Lactococcus lactis coexpressing antigen and cytokine*, Infect. Immun., 1998; 66:3183-9.
Medaglini, D., et al., *Mucosal and systemic immune responses to a recombinant protein expressed on the surface of the oral commensal bacterium Streptococcus gordonii after oral colonization*, Proc. Natl. Acad. Sci. USA, 1995; 92:6868-72. McCracken V.J. and Gaskins H.R., 'Probiotics a critical review', Horizon Scientific Press, UK 1999, p. 278.
Marson, A., et al., *Foxp3 occupancy and regulation of key target genes during T-cell stimulation*, Letters to Nature, 2007.

* cited by examiner

*Primary Examiner* — Anand Desai
*Assistant Examiner* — Iqbal H Chowdhury
(74) *Attorney, Agent, or Firm* — Waddey & Patterson, P.C.; James R. Cartiglia; Rebecca M. Barnett

(57) ABSTRACT

The present invention is directed to an infant formula or children's nutritional product comprising a protein source, a fat source, a carbohydrate source, and *B. longum* AH1205.

15 Claims, 7 Drawing Sheets

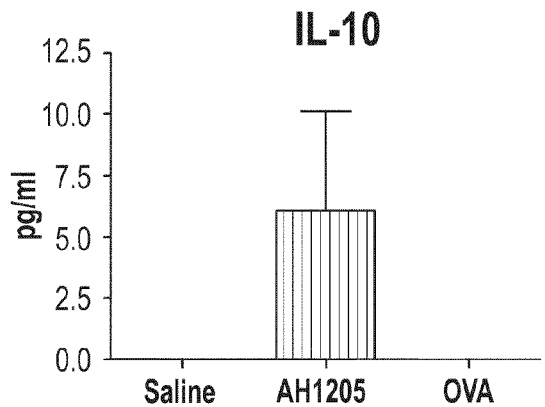
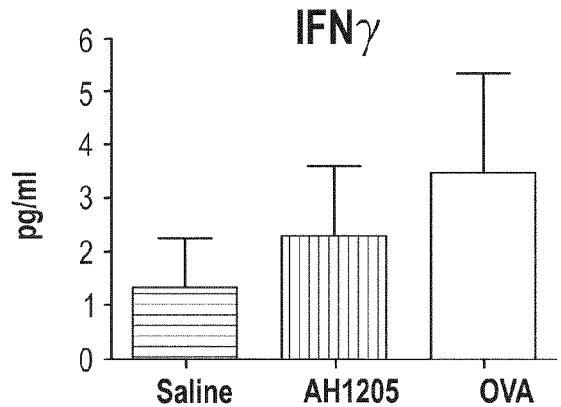
FIG. 6A    FIG. 6B
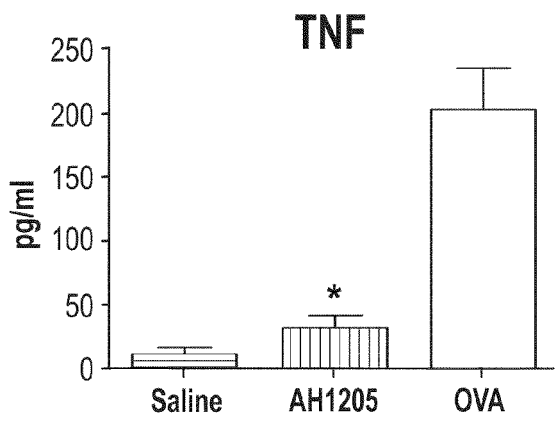
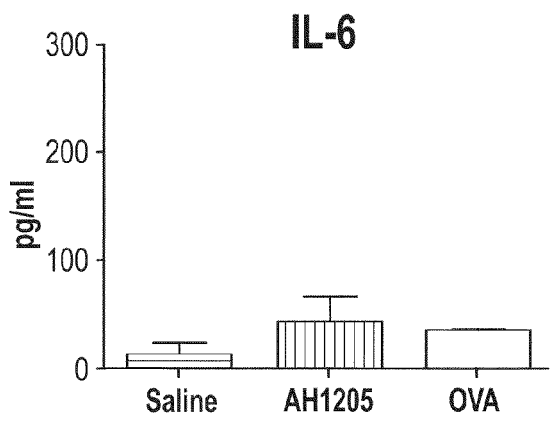
FIG. 6C    FIG. 6D
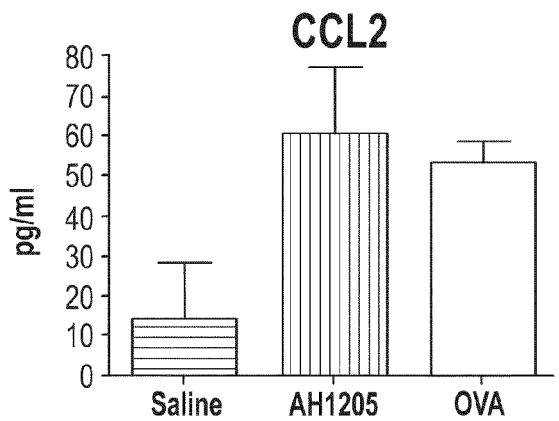
FIG. 6E

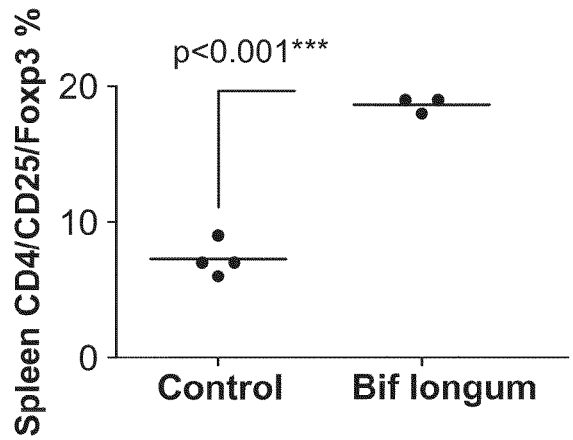
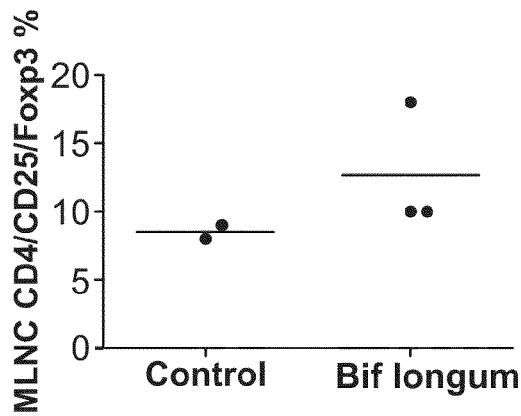
*FIG. 9A*  *FIG. 9B*
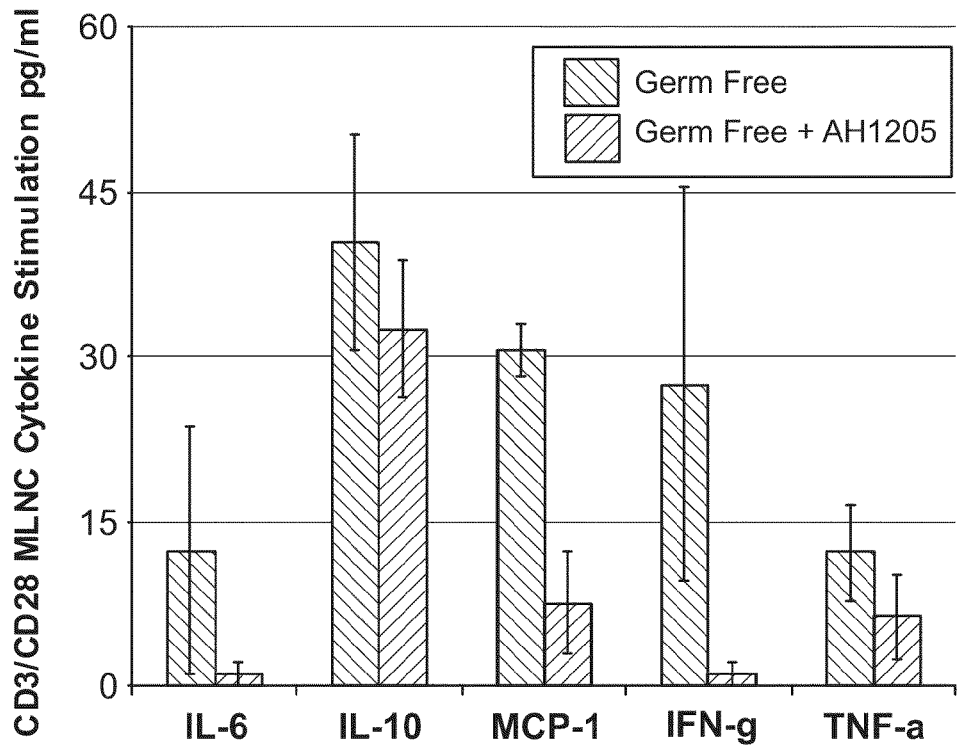
*FIG. 10*

SEQUENCE LISTING

<160> NUMBER OF SEQ ID NOS: 5

<210> SEQ ID NO 1
<211> LENGTH: 494
<212> TYPE: DNA
<213> ORGANISM: Bifidobacterium longum
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (263)..(263)

-continued

```
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (465)..(465)
```

```
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (489)..(491)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t

<400> SEQUENCE: 1
gcctagnctt ncngncacac gtcaccacac ggtgtcgcat ggccccgntn ggcatccttc      60
ctagcaaatt cccaggacga caaatcatca cactaaaatg atcacaaaac gatcgaaaca     120
aacactaaaa atagagtttng attngaaatt aacagcaaga acgaggaatn aaaggnaacc    180
ccgtnttgnt tgngtccact atncagtttt naagccacca cgcaccacca cgccgtncgg    240
acgggaccag cccgccatna ggnacgatgg gcatngaatc gcgccaggnc aaanccrggg    300
gtggcgatnc gggagcccaa aagcgcatnc acaccactnc cgcggaacat nccacgacgg    360
acgcaccgna agnccatgat tttttncaca ccancagccc caagncgccg cgactgncgc    420
gacgccnggg ctcgcaccgc cngacgaaca tncggncgtn ttntncgtan aaaggaggtt    480
cccancnann ncng                                                       494

<210> SEQ ID NO 2
<211> LENGTH: 479
<212> TYPE: DNA
<213> ORGANISM: Bifidobacterium longum
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
```

```
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (413)..(414)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
```

<221> NAME/KEY: misc_feature
<222> LOCATION: (473)..(473)
<223> OTHER INFORMATION: n is a, c, g, or t

<400> SEQUENCE: 2

```
aananaaacg ccgcngttct ccgcggtgcg tgccccgtcg tcncggcagt cgcggcggcc      60
tggggctgct ggtgtggaag agatcatggg ctttcggtgc gtccgtcntg ggatgttccg     120
cgggagtggt gtgnatgcgc ttttggnctc ccggatcgcc accncaggct ttggcctggc     180
gcgattcgat gcccatcgtg cctgatggcg ggctggtccc gtccggacgg cntggtggtg     240
cgtggtggct tgagaactgg atagtggacg cgagcaagac ngggtttcct ttgattcctc     300
ttcttgctgt tgatttcgaa tcgaactcta tttttantgt ttgnttccat cgttttgtga     360
ncattttaat gtgangantt gtcctctggg aatttgctan gaangancct tgnngccang     420
cncaccntgn ngnncctgtt gcctgcaang gcgnanggng gaagcccttg canccagaa     479
```

<210> SEQ ID NO 3
<211> LENGTH: 18
<212> TYPE: DNA
<213> ORGANISM: Unknown
<220> FEATURE:
<223> OTHER INFORMATION: Synthesized

<400> SEQUENCE: 3

```
gctggatcac ctcctttc                                                    18
```

<210> SEQ ID NO 4
<211> LENGTH: 18
<212> TYPE: DNA
<213> ORGANISM: Unknown
<220> FEATURE:
<223> OTHER INFORMATION: Synthesized

<400> SEQUENCE: 4

```
ctggtgccaa ggcatcca                                                    18
```

<210> SEQ ID NO 5
<211> LENGTH: 22
<212> TYPE: DNA
<213> ORGANISM: Unknown
<220> FEATURE:
<223> OTHER INFORMATION: Synthesized

<400> SEQUENCE: 5

```
ctacggcaag gcgacgctga cg                                               22
```

PROBIOTIC INFANT PRODUCTS

BACKGROUND OF THE INVENTION

Field of the Invention

The present invention relates generally to probiotic infant formulas and children's nutritional products.

SUMMARY OF THE INVENTION

Briefly, the present invention is directed, in an embodiment, to an infant formula or children's nutritional product comprising a protein source, a fat source, a carbohydrate source, and B. longum AH1205.

In another embodiment, the present invention is directed to a method for reducing inflammation in an infant or child comprising administering B. longum AH1205 to the infant or child.

BRIEF DESCRIPTION OF THE DRAWINGS

For a more complete understanding of the present invention, reference is now made to the following descriptions taken in conjunction with the accompanying drawings.

FIG. 6 A through E are graphs showing (A) IL-10, (B) interferon (IFN)-γ, (C) tumor necrosis factor (TNF)-α, (D) IL-6, and (E) chemokine (C—C motif) ligand 2 (CCL2) levels in BAL fluid from OVA-sensitized mice. Each column represents the mean±SEM (n=10, *p<0.05 compared to OVA-challenged, saline treated control);

FIGS. 9 A and B are graphs showing the percentage of CD4$^+$/CD25$^+$ cells expressing the transcription factor FoxP3. The figure shows that FoxP3 was significantly upregulated in germ-free mice consuming B. longum AH1205. (A)=spleen cells, (B)=mesenteric lymph node cells (MLNC) (n=4/group for spleen assay, n=2/3 for MLNC assay);

FIG. 10 is a graph showing that the level of cytokines IL-6, monocyte chemoattractant protein (MCP)-1 and IFN-γ secreted by CD3/CD28 stimulated MLNC cultures was reduced when germ-free mice consumed B. longum AH1205. Results are expressed as the mean per group±SEM (n=4/group);

DETAILED DESCRIPTION OF THE PREFERRED EMBODIMENTS

Figure 1:
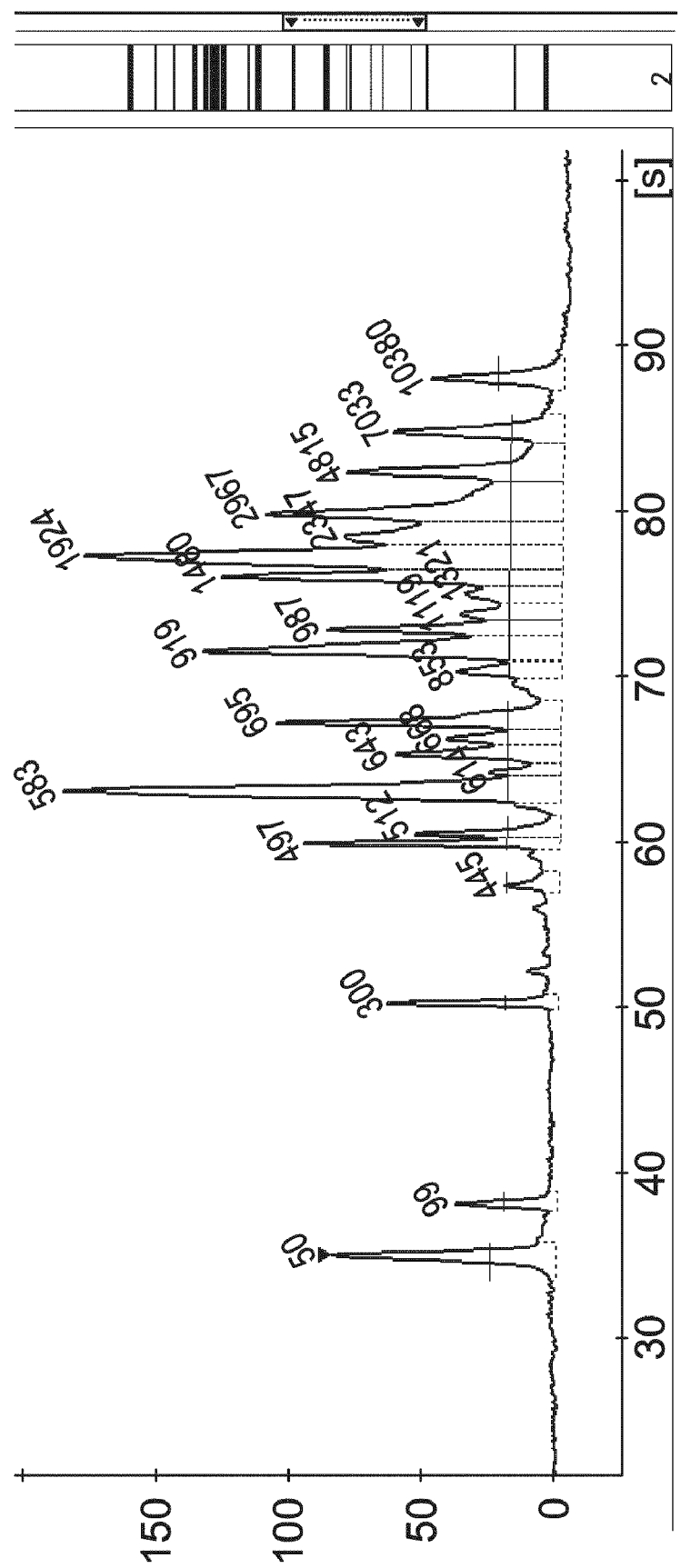
FIG. 1 is a BOX polymerase chain reaction (BOX PCR) (bioanalyzer) barcode profile for B. longum AH1205. Base pair sizes were determined using the Agilent 2100 software.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As set forth above, the present invention relates generally to probiotic infant formulas and children's nutritional products. References related to probiotic infant formulas and children's nutritional products may include U.S. Pat. Nos. 7,179,460 to Dennen, et al. and 5,922,375 to Luchansky, et al.

The technical problem to be solved by the present invention is to provide infant formulas and children's nutritional products containing novel probiotics. Thus, in an embodiment, the present invention is directed to an infant formula or children's nutritional product containing Bifidobacterium longum strain AH1205. A deposit of B. longum strain AH1205 was made at the National Collections of Industrial, Marine, and Food Bacteria (NCIMB), Scotland, UK, on May 11, 2006 and was accorded the accession number NCIMB 41387. The NCIMB is an International Depositary Authority recognized under the Budapest Treaty. The strain is acid and bile tolerant and transits the gastrointestinal tract. In a particular embodiment of the invention, B. longum AH1205 is isolated from infant feces.

In another embodiment, the infant formula or children's nutritional product contains B. longum strain AH1205 or a mutant or variant thereof. The mutant may be a genetically modified mutant. The variant may be a naturally occurring variant of Bifidobacterium. In some embodiments, the strain may be a probiotic. In other embodiments, the strain may be in the form of a biologically pure culture. In still other embodiments, the strain is an isolated strain.

As used herein, the terms "mutant", "variant", and "genetically modified mutant" include a strain of Bifidobacteria whose genetic and/or phenotypic properties are altered compared to the parent strain. Naturally occurring variants of *Bifidobacterium longum* include the spontaneous alterations of targeted properties selectively isolated. Deliberate alteration of parent strain properties is accomplished by conventional (in vitro) genetic manipulation technologies, such as gene disruption and conjugative transfer.

Genetic modification includes introduction of exogenous and/or endogenous DNA sequences into the genome of a Bifidobacteria strain, for example by insertion into the genome of the bacterial strain by vectors, including plasmid DNA, or bacteriophages. Natural or induced mutations include at least single base alterations such as deletion, insertion, transversion or other DNA modifications which may result in alteration of the amino acid sequence encoded by the DNA sequence.

The terms "mutant", "variant", and "genetically modified mutant" also include a strain of Bifidobacteria that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism, but whose products can be used for identification or selection of the bacterium, for example antibiotic resistance.

A person skilled in the art appreciates that mutant or variant strains of Bifidobacteria can be identified by DNA sequence homology analysis with the parent strain. Strains of Bifidobacteria having a close sequence identity with the parent strain are considered to be mutant or variant strains. A Bifidobacteria strain with a sequence identity (homology) of 96% or more, such as 97% or more, or 98% or more, or 99% or more with the parent DNA sequence may be considered to be a mutant or variant. Sequence homology may be determined using the on-line homology algorithm Basic Local Alignment Search Tool, called the "BLAST" program, which is publicly available at the National Center for Biotechnology Information in Bethesda, Md. USA.

Mutants of the parent strain also include derived Bifidobacteria strains having at least 85% sequence homology, such as at least 90% sequence homology, or at least 95% sequence homology to the 16 s-23 s intergenic spacer polynucleotide sequence of the parent strain. These mutants may further comprise DNA mutations in other DNA sequences in the bacterial genome.

In one embodiment of the invention, the *Bifidobacterium* strain is in the form of viable cells. Alternatively, the *Bifidobacterium* strain may be in the form of inactivated cells. The term "inactivated" means that the metabolic activity or reproductive ability of the strain has been reduced or destroyed. Inactivation may occur through any method currently known in the art or yet to be developed. The inactivation may be accomplished, for example, via heat treatment, lyophilization, ultraviolet light, gamma radiation, pressure, chemical disruption, mechanical disruption, or alteration of pH. For example, the probiotic may be inactivated with heat treatment via storage in the range of 80° C. to 100° C. for 10 minutes. The probiotic may also be inactivated with ultraviolet light via irradiation for 5 minutes at a distance of 5 cm from a 30 Watt UVC lamp. Alternatively, the probiotic may be inactivated with gamma radiation via irradiation with 2 kg-Gray (kGy) using a Cobalt-60 source at a distance of 20 cm. As used herein, the term "inactivated" is synonymous with "non-viable".

In an embodiment, *B. longum* strain AH1205 may be supplemented into a formulation for children or infants. The term "infant" means a postnatal human that is less than about 1 year old. The term "child" means a human in the age range of about 1 and 12 years old. In certain embodiments, a child is in the age range of about 1 and 6 years old. In other embodiments, a child is in the age range of about 7 and 12 years old.

The amount of *B. longum* AH1205 supplemented into the formulation of the invention may correspond to the range of about $1 \times 10^4$ to about $1 \times 10^{12}$ colony forming units (cfu) per gram formulation. In another embodiment, the amount supplemented into the formulation of the invention may correspond to the range of about $1 \times 10^6$ and about $1 \times 10^9$ cfu per gram formulation. In another embodiment, the amount supplemented into the formulation of the invention may correspond to the range of about $1 \times 10^9$ and about $1 \times 10^{12}$ cfu per gram formulation. In another embodiment, the amount supplemented into the formulation of the invention may correspond to at least about $1 \times 10^6$ cfu per gram formulation.

The form of administration of *B. longum* AH1205 in the present invention is not critical, as long as an effective amount is administered to a child or infant. In some embodiments, *B. longum* AH1205 is administered to a child or infant via tablets, pills, encapsulations, caplets, gelcaps, capsules, oil drops, sachets, liquids, liquid concentrates, powders, elixirs, solutions, suspensions, emulsions, lozenges, beads, and combinations thereof. In another embodiment, *B. longum* AH1205 is encapsulated in a sugar, fat, or polysaccharide. In yet another embodiment, *B. longum* AH1205 is added to a food or drink product and consumed. The food or drink product may be a nutritional supplement or a children's nutritional product such as a follow-on formula, growing up milk, beverage, milk, yoghurt, fruit juice, fruit-based drink, chewable tablet, cookie, cracker, or a milk powder.

In other embodiments, the product may be an infant's nutritional product, such as an infant formula or a human milk fortifier. As used herein, the term "infant formula" means a composition that satisfies the nutrient requirements of an infant by being a substitute for human milk. The term "human milk fortifier" means a composition which can be added to human milk to enhance the nutritional value of the human milk. In some embodiments, the composition is an acidified product (as required by certain medical food regulations).

The nutritional product may be a product for a full-term infant, a preterm infant, a low-birth-weight infant, or a very-low-birth-weight infant. As used herein, the terms "preterm" or "preterm infant" may include low-birth-weight infants or very-low-birth weight infants. Low-birth-weight infants are those born from about 32 to about 37 weeks of gestation or weighing from about 3.25 to about 5.5 pounds at birth. Very-low-birth-weight infants are those born before about 32 weeks of gestation or weighing less than about 3.25 pounds at birth. Thus, preterm infants may include infants born before about 37 weeks gestation and/or those weighing less than about 5.5 pounds at birth.

In certain embodiments, the formulations may be administered enterally or parenterally. As used herein, "enteral" means through or within the gastrointestinal, or digestive, tract, and "enteral administration" includes oral feeding, intragastric feeding, transpyloric administration, or any other introduction into the digestive tract. The term "parenterally"

means taken into the body or administered in a manner other than through the digestive tract, such as by intravenous or intramuscular injection.

The formulations of the invention may provide minimal, partial, or total nutritional support. The compositions may be nutritional supplements or meal replacements. In some embodiments, the compositions may be administered in conjunction with a food or nutritional composition. In this embodiment, the compositions can either be intermixed with the food or nutritional composition prior to ingestion by the subject or can be administered to the subject either before or after ingestion of a food or nutritional composition. The compositions may be administered to preterm infants receiving infant formula, breast milk, a human milk fortifier, or combinations thereof. The compositions may, but need not, be nutritionally complete. By the term "nutritionally complete," it is meant that the composition contains adequate nutrients to sustain healthy human life for extended periods.

In some embodiments, the invention may comprise a prenatal dietary supplement to be consumed by a pregnant woman, thereby providing B. longum AH1205 to the fetus in utero. In other embodiments, the invention may comprise a postnatal dietary supplement to be consumed by a nursing mother, thereby providing B. longum AH1205 to the postnatal infant via mother's milk.

If B. longum AH1205 is administered via an infant formula or children's nutritional product, the formulation may be nutritionally complete and contain suitable types and amounts of lipid, carbohydrate, protein, vitamins and minerals. The amount of lipid or fat typically may vary from about 3 to about 7 g/100 kcal. Lipid sources may be any known or used in the art, e.g., milk fat, egg yolk lipid, fish oil, vegetable oils such as palm oil, soybean oil, palmolein, palm oil, palm kernel oil, coconut oil, medium chain triglyceride oil, high oleic sunflower oil, olive oil, high oleic safflower oil, and esters of fatty acids.

The amount of protein typically may vary from about 1 to about 5 g/100 kcal. Protein sources may be any known or used in the art, e.g., milk protein, non-fat milk solids, nonfat milk, whey protein, casein, soy protein, animal protein, cereal protein, vegetable protein, or combinations thereof. The formulation may contain proteins and/or peptides rich in glutamine/glutamate. The protein source may be intact, partially hydrolyzed, or extensively hydrolyzed. The protein source, in some embodiments, may be a combination of intact protein and hydrolyzed protein. The protein source may be an isolate or a concentrate.

In certain embodiments, the composition of the invention may contain a nitrogen source (i.e., amino acids and/or protein) such that the total amount of amino acids or protein may be from about 1 g/100 kilocalories (kcal) to about 10 g/100 kcal of total composition, in some embodiments about 2 g/100 kcal to about 6 g/100 kcal. The amount of lipid source per 100 kcal of total composition may be greater than 0 g up to about 6 g, in some embodiments about 0.5 g to about 5.5 g, and in other embodiments about 2 g to about 5.5 g; and the amount of non-fiber carbohydrate source per 100 kcal of total composition may be about 5 g to about 20 g, and in some embodiments may be about 7.5 g to about 15 g. The amount of vitamins and minerals in the nutritionally complete composition may be sufficient to meet 100% of the U.S. recommended daily intake (RDI) of about 500 to about 3,000 kcal, in some embodiments about 1,000 to about 3,000 kcal. In a particular embodiment, the composition may be protein-free. In such an embodiment, the composition may contain a protein equivalent source that comprises 100% free amino acids.

The amount of carbohydrate typically may vary from about 8 to about 12 g/100 kcal. Carbohydrate sources may be any known or used in the art, e.g., lactose, fructose, glucose, corn syrup, corn syrup solids, maltodextrins, sucrose, starch, rice syrup solids, rice starch, modified corn starch, modified tapioca starch, rice flour, soy flour, and combinations thereof. The formulation may include any one or more of an adjuvant, a bacterial component, a drug entity, or a biological compound.

Conveniently, commercially available infant formulas and other formulations may be used in practice of the present invention. For example, Enfamil®, Enfamil® Premature Formula, Enfamil® with Iron, Lactofree®, Nutramigen®, Pregestimil®, and ProSobee® (available from Mead Johnson & Company, Evansville, Ind., U.S.A.) may be supplemented with suitable levels of B. longum AH1205 and used in practice of the invention.

The formulation of the present invention may optionally include one or more of the following vitamins or derivatives thereof, including, but not limited to, biotin, vitamin $B_1$, thiamin, thiamin pyrophosphate, vitamin $B_2$, riboflavin, flavin mononucleoride, flavin adenine dinucleotide, pyridoxine hydrochloride, thiamin mononitrate, folic acid, vitamin $B_3$, niacin, nicotinic acid, nicotinamide, niacinamide, nicotinamide adenine dinucleotide, tryptophan, biotin, pantothenic acid, vitamin $B_6$, vitamin $B_{12}$, cobalamin, methylcobalamin, deoxyadenosylcobalamin, cyanocobalamin, calcium pantothenate, pantothenic acid, vitamin C, ascorbic acid, vitamin A, retinol, retinal, retinoic acid, beta-carotene, vitamin D, vitamin $D_3$, calciferol, cholecalciferol, dihydroxy vitamin D, 1,25-dihydroxycholecalciferol, 7-dehyrdocholesterol, choline, vitamin E, vitamin E acetate, vitamin K, menadione, menaquinone, phylloquinone, naphthoquinone, and mixtures thereof.

The formulation of the present invention may optionally include one or more of the following minerals or derivatives thereof, including, but not limited to, phosphorus, potassium, sulfur, sodium, docusate sodium, chloride, manganese, magnesium, magnesium stearate, magnesium carbonate, magnesium oxide, magnesium hydroxide, magnesium sulfate, copper, cupric sulfate, iodide, boron, zinc, zinc oxide, chromium, molybdenum, iron, carbonyl iron, ferric iron, ferrous fumarate, polysaccharide iron, fluoride, selenium, molybdenum, calcium phosphate or acetate, potassium phosphate, magnesium sulfate or oxide, sodium chloride, potassium chloride or acetate, ferric orthophosphate, alpha-tocopheryl acetate, zinc sulfate or oxide, copper gluconate, chromium chloride or picolonate, potassium iodide, sodium selenate, sodium molybdate, phylloquinone, cyanocobalamin, sodium selenite, copper sulfate, inositol, potassium iodide, cobalt, and mixtures thereof. Non-limiting exemplary derivatives of mineral compounds include salts, alkaline salts, esters and chelates of any mineral compound.

The composition of the invention also may contain emulsifiers and stabilizers such as soy lecithin, carrageenan, and combinations thereof. The composition of the invention may optionally contain other substances that may have a beneficial effect such as lactoferrin, nucleotides, nucleosides, immunoglobulins, and combinations thereof.

In one embodiment of the invention, B. longum AH1205 may be administered in combination with one or more probiotics. The term "probiotic" means a micro-organism that exerts beneficial effects on the health of the host. Any probiotic known in the art may be acceptable in this embodiment provided it achieves the intended result. In a particular embodiment, the probiotic may be selected from LGG, Bifidobacterium longum species, and Bifidobacterium animalis subsp. *lactis* BB-12. In an embodiment, the additional probiotic(s) may be viable or non-viable.

In another embodiment of the invention, *B. longum* AH1205 may be combined with one or more prebiotics. The term "prebiotic" means a non-digestible food ingredient that stimulates the growth and/or activity of probiotics. Any prebiotic known in the art will be acceptable in this embodiment provided it achieves the desired result. Prebiotics useful in the present invention may include oligosaccharides, polysaccharides, and other prebiotics that contain fructose, xylose, soya, galactose, glucose and mannose. More specifically, prebiotics useful in the present invention may include lactulose, gluco-oligosaccharide, inulin, polydextrose, galacto-oligosaccharide, fructo-oligosaccharide, isomalto-oligosaccharide, soybean oligosaccharides, lactosucrose, xylo-oligosacchairde, and gentio-oligosaccharides.

In yet another embodiment of the present invention, the formulation may contain other active agents such as long chain polyunsaturated fatty acids (LCPUFAs). Suitable LCPUFAs include, but are not limited to, α-linoleic acid, γ-linoleic acid, linoleic acid, linolenic acid, eicosapentanoic acid (EPA), arachidonic acid (ARA) and/or docosahexaenoic acid (DHA). In an embodiment, *B. longum* AH1205 is administered in combination with DHA. In another embodiment, *B. longum* AH1205 is administered in combination with ARA. In yet another embodiment, *B. longum* AH1205 is administered in combination with both DHA and ARA. Commercially available infant formula that contains DHA, ARA, or a combination thereof may be supplemented with *B. longum* AH1205 and used in the present invention. For example, Enfamil® LIPIL®, which contains effective levels of DHA and ARA, is commercially available and may be supplemented with *B. longum* AH1205 and utilized in the present invention.

In one embodiment, both DHA and ARA are administered in combination with *B. longum* AH1205. In this embodiment, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

In certain embodiments of the invention, the level of DHA is in the range of about 0.0% and 1.00% of fatty acids, by weight. The level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

In embodiments of the invention, the level of ARA is in the range of 0.0% and 0.67% of fatty acids, by weight. In another embodiment, the level of ARA may be about 0.67% by weight. In another embodiment, the level of ARA may be about 0.5% by weight. In yet another embodiment, the level of DHA may be in the range of about 0.47% and 0.48% by weight.

If included, the effective amount of DHA in an embodiment of the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

If included, the effective amount of ARA in an embodiment of the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If an infant formula is utilized, the amount of DHA in the infant formula may vary from about 5 mg/100 kcal to about 80 mg/100 kcal. In one embodiment of the present invention, DHA varies from about 10 mg/100 kcal to about 50 mg/100 kcal; and in another embodiment, from about 15 mg/100 kcal to about 20 mg/100 kcal. In a particular embodiment of the present invention, the amount of DHA is about 17 mg/100 kcal.

If an infant formula is utilized, the amount of ARA in the infant formula may vary from about 10 mg/100 kcal to about 100 mg/100 kcal. In one embodiment of the present invention, the amount of ARA varies from about 15 mg/100 kcal to about 70 mg/100 kcal. In another embodiment, the amount of ARA varies from about 20 mg/100 kcal to about 40 mg/100 kcal. In a particular embodiment of the present invention, the amount of ARA is about 34 mg/100 kcal.

If an infant formula is used, the infant formula may be supplemented with oils containing DHA and ARA using standard techniques known in the art. For example, DHA and ARA may be added to the formula by replacing an equivalent amount of an oil, such as high oleic sunflower oil, normally present in the formula. As another example, the oils containing DHA and ARA may be added to the formula by replacing an equivalent amount of the rest of the overall fat blend normally present in the formula without DHA and ARA.

If utilized, the source of DHA and ARA may be any source known in the art such as marine oil, fish oil, single cell oil, egg yolk lipid, and brain lipid. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

In one embodiment, a LCPUFA source which contains EPA is used in combination with *B. longum* AH1205. In another embodiment, a LCPUFA source which is substantially free of EPA is used in combination with *B. longum* AH1205. For example, in one embodiment of the present invention, an infant formula containing less than about 16 mg EPA/100 kcal is supplemented with *B. longum* AH1205 and used in the method of the present invention. In another embodiment, an infant formula containing less than about 10 mg EPA/100 kcal is supplemented with *B. longum* AH1205 and used in the method of the present invention. In yet another embodiment, an infant formula containing, less than about 5 mg EPA/100 kcal is supplemented with *B. longum* AH1205 and used in the method of the present invention. Another embodiment of the invention includes an infant formula supplemented with *B. longum* AH1205 that is free of even trace amounts of EPA.

It will be appreciated that the combination of *B. longum* AH1205 and probiotics, prebiotics, LCPUFAs or other active ingredients may be administered in a single formulation or as separate formulations administered at the same or different times and using the same or different routes of administration.

In one embodiment of the invention, the formulation may be used in immunization and vaccination protocols. Oral immunization using probiotic bacteria as vectors would not only protect the host from infection, but may replace the immunological stimuli that the pathogen would normally elicit, thus contributing to the immunological education of the host.

In an embodiment of the invention, the formulation is useful in treating, reducing, and/or preventing inflammation. As used herein, the term "treating" means ameliorating, improving or remedying a disease, disorder, or symptom of a disease or condition. The term "reducing" means to diminish in extent, amount, or degree. The term "preventing" means to stop or hinder a disease, disorder, or symptom of a disease or condition through some action.

In a particular embodiment, the invention comprises the use of *B. longum* AH1205 for the manufacture of a composition for reducing inflammation in an infant or child. Examples 2-5 each indicate that administration of *B. longum* AH1205 may reduce or prevent inflammation in an infant or child. The inflammation may be reduced in the gastrointestinal tract, the respiratory tract, or may be reduced systemically. The reduction of inflammation may improve allergies or asthma.

In this embodiment, the inflammation may be respiratory inflammation, such as asthma, allergic rhinitis, sinusitis, airway tissue inflammation, upper respiratory infection, influenza, croup, respiratory syncytial virus, bronchitis, bronchiolitis, pneumonia, or airway lumen inflammation. Similarly, the inflammation may be gastrointestinal inflammation, such as diarrhea, inflammatory bowel disease, Crohn's disease, enterocolitis, ulcerative colitis, allergic colitis, irritable bowel syndrome, pouchitis, post-infection colitis, *Clostridium difficile*-associated diarrhea, Rotavirus-associated diarrhea, or post-infective diarrhea, or diarrheal disease due to an infectious agent, such as *E. coli*. In other embodiments, the inflammation may be systemic, such as in rheumatoid arthritis. The term "systemic", as used herein, means relating to or affecting the entire body.

In some embodiments, the reduction or prevention of inflammation may ameliorate or prevent atopic conditions or diseases. For example, the reduction or prevention of inflammation may ameliorate or prevent atopic dermatitis. In a particular embodiment, the reduction or prevention of inflammation may ameliorate or prevent common infant or childhood illnesses. For example, the reduction or prevention of inflammation may ameliorate or prevent diarrhea or acute otitis media. In yet another embodiment, the reduction or prevention of inflammation may ameliorate or prevent food allergies.

It is believed that *B. longum* AH1205 acts by antagonizing and excluding pro-inflammatory micro-organisms from the gastrointestinal tract or inflammatory site. It is also believed that *B. longum* AH1205 acts by reducing the levels of pro-inflammatory cytokines.

In a particular embodiment, the strain may modify the levels of IL-10 in a subject. IL-10 is produced by T cells, B cells, monocytes and macrophages. This cytokine augments the proliferation and differentiation of B cells into antibody secreting cells. IL-10 exhibits mostly anti-inflammatory activities. It up-regulates IL-1RA expression by monocytes and suppresses the majority of monocyte inflammatory activities. IL-10 inhibits monocyte production of cytokines, reactive oxygen and nitrogen intermediates, major histocompatibility complex (MHC) class II expression, parasite killing and IL-10 production via a feed back mechanism. This cytokine has also been shown to block monocyte production of intestinal collagenase and type IV collagenase by interfering with a prostaglandin E2-cyclic adenosine monophosphate ($PGE_2$-cAMP) dependant pathway and therefore may be an important regulator of the connective tissue destruction seen in chronic inflammatory diseases. Thus, in an embodiment, the strain may upregulate, or induce secretion of, IL-10 levels in infants or children consuming the strain.

In other embodiments, *B. longum* AH1205 downregulates or decreases secretion of TNF-$\alpha$, IL-6, MCP-1, and/or IFN-$\gamma$ or other pro-inflammatory cytokines or chemokines. TNF-$\alpha$, a pro-inflammatory cytokine, initiates a cascade of cytokines and biological effects resulting in an inflammatory state.

In some embodiments, the formulation of the invention is useful for maintaining the homeostasis of the immune system. In other embodiments, the formulation of the invention is useful for improving or enhancing immunity in a subject.

In some embodiments, the enhancement of immunity or suppression of inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T and B cell immunity; stimulation of a helper T cell 1 (Th1) cytokine pattern (increased IL-1, IL-2, IFN-$\gamma$, IL-12, TNF-$\alpha$; human leukocyte antigen-Dr (HLA-Dr) expression); suppression of inflammation or production of systemic and mucosal inflammatory mediators (including cytokines and/or chemokines); reduction of sensitization by reducing total and/or allergen-specific IgE; reduction of the production of allergic cytokines; reduction of a Th2 supporting immunoglobulin profile; and combinations thereof.

The production of multifunctional cytokines across a wide spectrum of tumor types suggests that significant inflammatory responses are ongoing in patients with cancer. Thus, in an embodiment of the invention, *B. longum* AH1205 may be useful in treating the symptoms of cancer. Due to the anti-inflammatory properties of *B. longum* AH1205, this bacterial strain may reduce the rate of malignant cell transformation. Furthermore, intestinal bacteria can produce, from dietary compounds, substances with genotoxic, carcinogenic and tumor-promoting activity and gut bacteria can activate procarcinogens to DNA reactive agents. In general, species of *Bifidobacterium* have low activities of xenobiotic metabolizing enzymes compared to other populations within the gut such as bacteroides, eubacteria and clostridia. Therefore, increasing the number of *Bifidobacterium* bacteria in the gut could beneficially modify the levels of these enzymes.

In particular embodiments, *B. longum* AH1205 may be administered in combination with anti-inflammatory therapies such as non-steroid anti-inflammatory drugs (NSAIDs) or infliximab.

The infant gut microflora is rapidly established in the first few weeks following birth. The nature of this intestinal colonization is initially determined by early exposure to environmental sources of microbes as well as the health of the infant. Infants born via cesarean section, preterm or other infants who spend the first portion of their lives in a sterile incubator, and/or infants that are administered antibiotics early in life are likely to have significant delays in the development of a healthy gut microflora. Because these infants do not have the opportunity to acquire a healthy gut microflora from their mothers or environment, consumption of *B. longum* AH1205 may beneficially contribute to the proper development and function of the intestinal immune system.

In some embodiments of the present invention, the infant or child is in need of the treatment, reduction, or prevention of inflammation. The subject may be at risk for inflammation due to genetic predisposition, diet, lifestyle, diseases, or disorders. For example, a preterm or immunosuppressed infant may be at risk for inflammation and may, therefore, be in need of such treatment, reduction, or prevention.

The composition of the invention can be packaged in any type of container known in the art to be used for storing nutritional products such as glass, lined paperboard, plastic, and coated metal cans. In some embodiments, the composition is packaged via blow-fill-seal packaging techniques. In other embodiments, the composition is provided in a single dose container. The packaging of the composition may be conducted under aseptic conditions. In some embodiments, the composition is prepared such that it is acceptable for direct delivery to a preterm infant via nasogastric tubes, nasoduodenal tubes, or nasojejunal tubes.

The composition of the invention may be shelf stable. By "shelf stable," it is meant that the composition, in a form that is ready to consume, remains in a single homogenous phase (i.e., does not separate into more than one phase upon visual inspection), and/or that settling does not occur upon visual inspection after storage overnight in the refrigerator.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example illustrates the characterization of bacteria isolated from infant feces.

Isolation of Probiotic Bacteria

Fresh feces were obtained from a 3-day old male breast-fed infant and serial dilutions were plated on TPY (trypticase, peptone and yeast extract) and MRS (deMann, Rogosa and Sharpe) media supplemented with 0.05% cysteine and mupirocin. Plates were incubated in anaerobic jars (BBL, Oxoid) using $CO_2$ generating kits (Anaerocult A, Merck) for 2-5 days at 37° C. Gram-positive, catalase negative rod-shaped or bifurcated/pleomorphic bacteria isolates were streaked for purity on to complex non-selective media (MRS and TPY). Isolates were routinely cultivated in MRS or TPY medium unless otherwise stated at 37° C. under anaerobic conditions. Presumptive *Bifidobacterium* were stocked in 40% glycerol and stored at −20° C. and −80° C.

Following isolation of a pure Bifidobacteria strain, assigned the designation AH1205, microbiological characteristics were assessed and are summarized in Table 1 below. AH1205 is a gram-positive, catalase-negative pleomorphic shaped bacterium which is Fructose-6-Phoshate Phosphoketolase positive confirming its identity as a *Bifidobacterium*. Using minimal media in which a single carbon source was inserted, AH1205 was able to grow on all carbon sources tested (Glucose, Lactose, Ribose, Arabinose, Galactose, Raffinose, Fructose, Malt Extract, Mannose, Maltose, Sucrose).

TABLE 1

Physiochemical characteristics of *B. longum* AH1205

|  | *B. longum* AH1205 |
| --- | --- |
| Strain Characteristics |  |
| Gram Stain | + |
| Catalase | − |
| Motility | − |
| F6PPK* | + |
| Milk coagulation | + |
| 45° C. anaerobic culture | − |
| 45° C. aerobic culture | − |
| Carbohydrate (CHO) Fermentation |  |
| Glucose | + |
| Lactose | + |
| Ribose | + |
| Arabinose | + |
| Galactose | + |
| Raffinose | + |
| Fructose | + |
| Malt Extract | + |
| Mannose | + |
| Maltose | + |
| Sucrose | + |

*signifies Fructose-6-Phoshate Phosphoketolase Assay

Species Identification 16 s intergenic spacer (IGS) sequencing was performed to identify the species of bifidobacteria isolated. Briefly, DNA was isolated from AH1205 using 100 µl of Extraction Solution and 25 µl of Tissue Preparation solution (Sigma, XNAT2 Kit). The samples were incubated for 5 minutes at 95° C. and then 100 µl of Neutralization Solution (XNAT2 kit) was added. Genomic DNA solution was quantified using a Nanodrop spectrophotometer and stored at 4° C. PCR was performed using the IGS primers, IGS L: 5'-GCTGGATCAC-CTCCTTTC-3' (SEQ ID NO. 3) which is based on SEQ ID NO. 1 and IGS R: 5'-CTGGTGCCAAGGCATCCA-3' (SEQ ID NO. 4) which is based on SEQ ID NO. 2. The cycling conditions were 94° C. for 3 min (1 cycle), 94° C. for 30 sec, 53° C. for 30 sec, 72° C. for 30 sec (28 cycles). The PCR reaction contained 4 µl (50 ng) of DNA, PCR mix (XNAT2 kit), 0.4 µM IGS L and R primer (MWG Biotech, Germany). The PCR reactions were performed on an Eppendorf thermocycler. The PCR products (10 µl) were run alongside a molecular weight marker (100 bp Ladder, Roche) on a 2% agarose EtBr stained gel in tris-acetate buffer (TAE), to determine the IGS profile. PCR products of *Bifidobacterium* (single band) were purified using the Promega Wizard PCR purification kit. The purified PCR products were sequenced using the primer sequences (above) for the intergenic spacer region. Sequence data was then searched against the National Center for Biotechnology Information (NCBI) nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/). The nearest match to the sequence was identified and then the sequences were aligned for comparison using DNASTAR MegAlign software. The sequences (SEQ ID NO. 1 [IGS forward sequence] and SEQ ID NO. 2 [IGS reverse sequence]) obtained can be viewed in the sequence listing. Searching the NCIMB database revealed that AH1205 has a unique IGS (SEQ ID NO. 1 [forward sequence] and SEQ ID NO. 2 [reverse sequence]) sequence with its closest sequence homology to a *Bifidobacterium longum*. A paper copy and computer readable format of the Sequence Listing for Table 3 have been submitted herewith and are hereby incorporated by reference in their entirety. The computer readable file on the disc is identified as AH1205_ST25.txt, Size: 3 KB, Created Sep. 12, 2008.

In order to develop a barcode PCR profile for AH1205, PCR was performed using BOX primers. The cycling conditions were 94° C. for 7 min (1 cycle); 94° C. for 1 minute, 65° C. for 8 minutes, (30 cycles) and 65° C. for 16 minutes. The PCR reaction contained 50 ng of DNA, PCR mix (XNAT2 kit) and 0.3 µM BOXA1R primer (5'-CTACGGCAAGGC-GACGCTGACG-3') (SEQ ID NO. 5) (MWG Biotech, Germany). The PCR reactions were performed on an Eppendorf thermocycler. The PCR products (1 µl) were run alongside a molecular weight marker (DNA 7500 ladder, Agilent, Germany) using the DNA 7500 LabChip® on the Agilent 2100 Bioanalyzer (Agilent, Germany). The barcode (PCR product profile) was determined using the Agilent Bioanalyzer software where peak number (PCR products) and size were identified (FIG. 1).

Antibiotic Sensitivity Profiles

Antibiotic sensitivity profiles of the *B. longum* strain were determined using the "disc susceptibility" assay. Cultures were grown in the appropriate broth medium for 24-48 hours, spread-plated (100 µl) onto agar media, and discs containing known concentrations of the antibiotics were placed onto the agar. Strains were examined for antibiotic sensitivity after 1-2 days incubation at 37° C. under anaerobic conditions. Strains were considered sensitive if zones of inhibition of 1 mm or greater were seen. The minimum inhibitory concentration (MIC) for each antibiotic was independently assessed. The MIC for clindamycin, vancomycin and metronidazole were 0.032, 0.75 and >256 respectively.

Intestinal Transit

To determine whether *Bifidobacterium longum* could survive at low pH values equivalent to those found in the stomach, bacterial cells were harvested from fresh overnight cultures, washed twice in phosphate buffer (pH 6.5), and resuspended in TPY broth adjusted to pH 2.5 (with 1M HCl). Cells were incubated at 37° C. and survival measured at intervals of 5, 30, 60 and 120 minutes using the plate count method. AH1205 survived well for 5 minutes at pH 2.5 while no viable cells were recovered after 30 minutes.

Upon exiting the stomach, putative probiotics are exposed to bile salts in the small intestine. In order to determine the ability of *B. longum* to survive exposure to bile, cultures were streaked on TPY agar plates supplemented with 0.3% (w/v), 0.5%, 1%, 2%, 5%, 7.5% or 10% porcine bile. *B. longum* AH1205 growth was observed on plates containing up to 0.5% bile.

Figure 2:
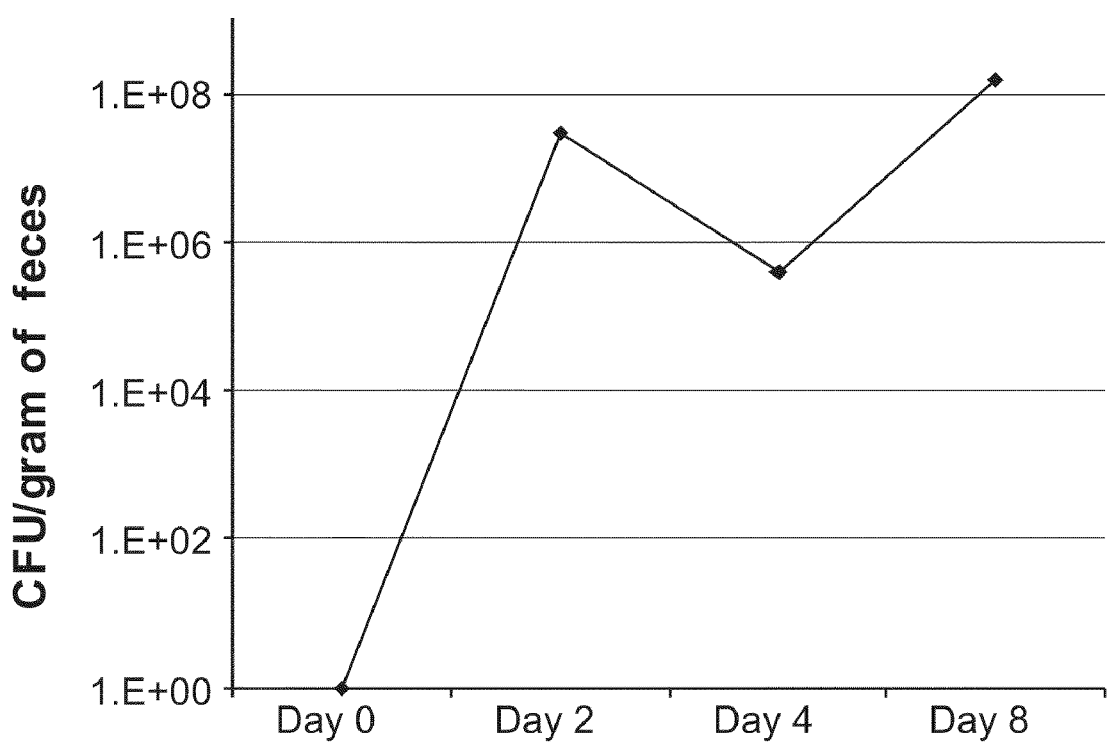
FIG. 2 is a graph illustrating the fecal recovery of B. longum AH1205 over an 8-day feeding period, which demonstrates the ability of AH1205 to transit the murine gastrointestinal tract.

In a murine model, the ability of *B. longum* AH1205 to transit the gastrointestinal tract was assessed. Mice consumed $1 \times 10^9$ AH1205 daily and fecal pellets were examined for the presence of the fed micro-organism. Detection of AH1205 was facilitated by isolating a spontaneous rifampicin resistant variant of the bifidobacteria-incorporation of rifampicin in the TPY plates used to assess transit ensured that only the fed rifampicin resistant bifidobacteria was cultured. Fecal samples were collected daily and *B. longum* transit through the gastrointestinal tract was confirmed (FIG. 2).

Anti-Microbial Activity

The indicator pathogenic micro-organisms used in this study were propagated in the following medium under the following growth conditions: *Salmonella typhimurium* (37° C., aerobic) in Tryptone Soya broth/agar supplemented with 0.6% yeast extract (TSAYE, Oxoid), *Campylobacter jejuni* (37° C., anaerobic) and *E. coli* O157:H7 (37° C., anaerobic) on Blood agar medium, and *Clostridium difficile* (37° C., anaerobic) in reinforced Clostridial medium (RCM, Oxoid). All strains were inoculated into fresh growth medium and grown overnight before being used in experiments.

Antimicrobial activity was detected using the deferred method. Briefly, *B. longum* AH1205 was incubated for 36-48 hours. Ten-fold serial dilutions were spread-plated (100 µl) onto TPY agar medium. After overnight incubation, plates with distinct colonies were overlayed with the indicator bacterium. The indicator lawn was prepared by inoculating a molten overlay with 2% (v/v) of an overnight indicator culture which was poured over the surface of the inoculated TPY plates. The plates were re-incubated overnight under conditions suitable for growth of the indicator bacterium. Indicator cultures with inhibition zones greater than 1 mm in radius were considered sensitive to the test bacterium. *B. longum* AH1205 inhibited the growth of all pathogenic organisms tested, with zones of clearing measuring 8.67, >80, 4.33, and 11.67 mm for *Salmonella typhimurium, Campylobacter jejuni, E. coli* O157:H7, and *Clostridium difficile* respectively.

EXAMPLE 2

Figure 3:
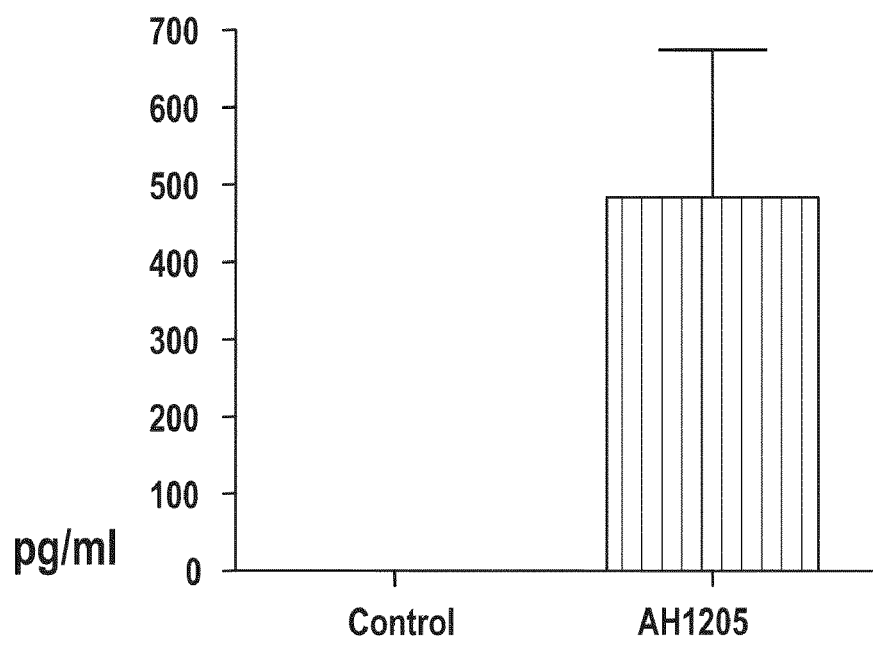
FIG. 3 is a bar graph showing the effect of B. longum AH1205 on interleukin (IL)-10 cytokine production by human peripheral blood mononuclear cells (PBMCs). Results are expressed as mean±standard error of measurement (SEM) (n=6)

This example illustrates cytokine production by PBMCs in response to *B. longum*. PBMCs were isolated from healthy donors by density gradient centrifugation. PBMCs were stimulated with the probiotic bacterial strain for a 72 hour period at 37° C. At this time, culture supernatants were collected, centrifuged, aliquoted and stored at −70° C. until being assessed for IL-10 levels using cytometric bead arrays (CBA) (BD BioSciences). AH1205 induced significant secretion of IL-10 by human PBMCs, suggesting this probiotic strain Would induce an anti-inflammatory response in vivo (FIG. 3). As an anti-inflammatory agent, it may be useful in reducing and preventing inflammation in humans.

EXAMPLE 3

This study investigated whether the probiotic bacteria *B. longum* AH1205 attenuates respiratory disease in a murine model of asthma. More specifically, *B. longum* AH1205 was investigated to determine if it would suppress allergic responses in an OVA-sensitized mouse model of allergic airway inflammation. Briefly, adult male BALB/c mice were sensitized by intraperitoneal (IP) injection of OVA at day 0 and day 6. On days 12 and 14, mice were challenged intranasally with OVA. Twenty-four hours after the last challenge (day 15), mice were subjected to measurements of airway responsiveness followed by BAL procedure. OVA/alum-sensitized, saline-challenged mice served as controls. Animals received probiotic or placebo throughout the trial. Airway inflammation (cytokine and cell count) was assessed by inflammatory cell counts in BAL fluid. Airway responsiveness was also measured using the Buxco whole-body plethysmograph. Splenocytes were also isolated from OVA-sensitized mice and were incubated in the presence of anti-CD3 and anti-CD28 antibodies after which cytokine levels were measured in the supernatants by flow cytometry.

Figure 4A:
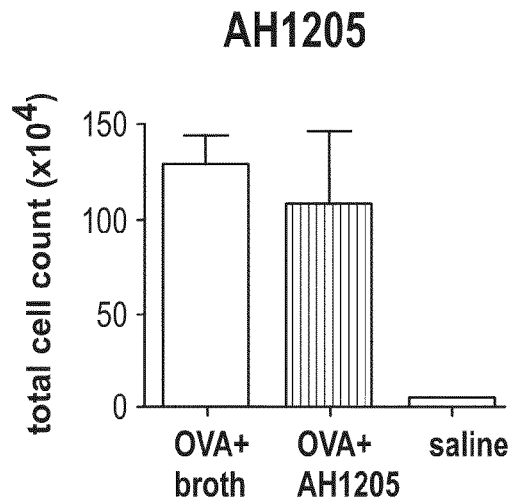
FIGS. 4 A and B are graphs showing the effect of (A) B. longum AH1205 and (B) placebo on total cell numbers in bronchoalveolar lavage (BAL) fluid following ovalbumin (OVA) challenge in sensitized animals (n=10/group, *=p<0.05 compared to OVA challenge alone)
Figure 4B:
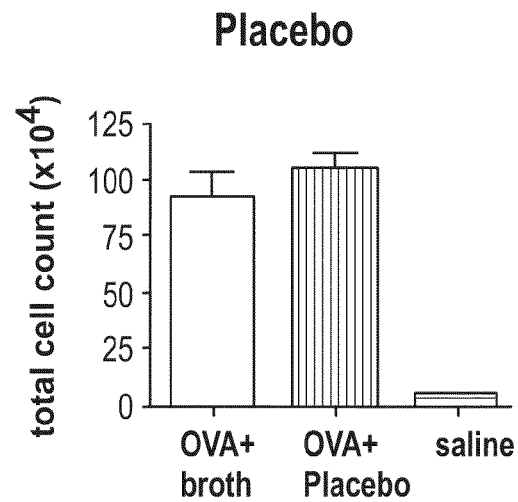
Figure 5A:
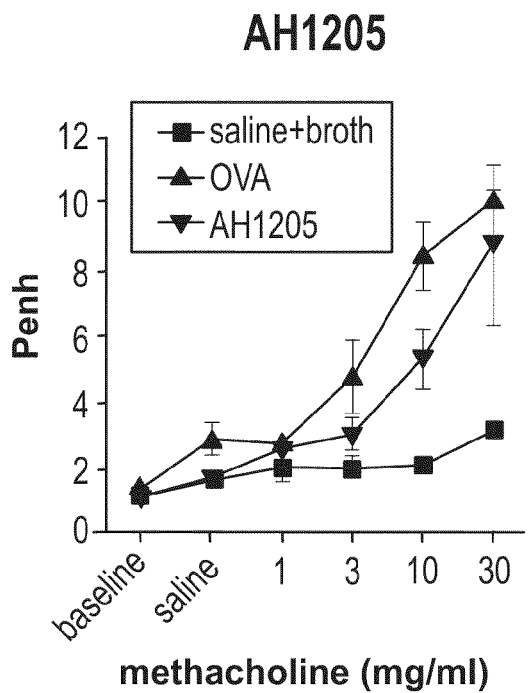
FIGS. 5 A and B are graphs showing the effect of (A) B. longum AH1205 treatment and (B) placebo on airway responsiveness to methacholine, as assessed by changes in enhanced pause (Penh) in OVA-sensitized mice 24 hours after intranasal challenge with OVA or saline. Each data point represents the mean±SEM (n=10/groups*p=<0.05 compared to OVA alone)
Figure 5B:
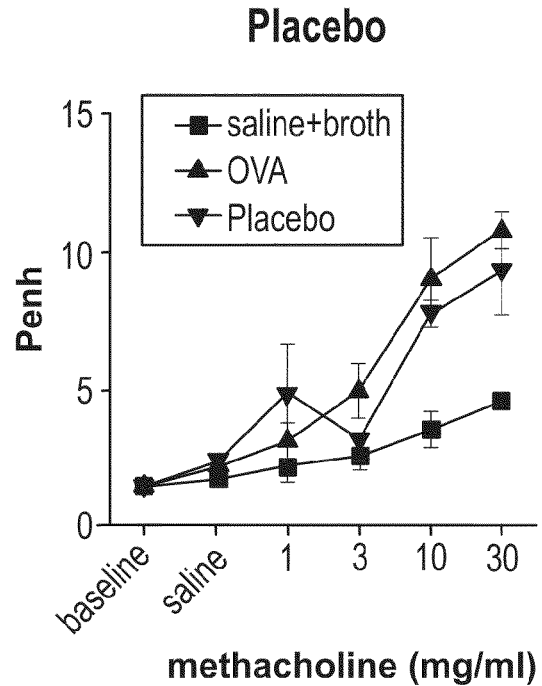

*B. longum* AH1205 caused no significant reduction in cells recovered from BAL fluid following OVA challenge, when compared to broth fed animals (FIG. 4). Airway responsiveness was measured and a challenge of sensitized mice with OVA resulted in an enhancement of AHR to methacholine when compared with saline-challenged mice. AH1205 did not modulate this enhanced airway responsiveness to methacholine, as assessed by changes in enhanced pause (FIG. 5).

BAL cytokine levels were measured by CBA and demonstrated that animals fed AH1205 had significantly reduced TNF-α levels compared to OVA control (FIG. 6C). This reduction of TNF-α levels suggests that *B. longum* AH1205 may attenuate or prevent respiratory disease and suppress or prevent allergic responses. No significant differences were noted for IL-10, IFN-γ, IL-6 and CCL2 levels. (FIG. 6).

EXAMPLE 4

This study investigated the effect of probiotic consumption on regulatory T cell number and activity in healthy mice. BALB/c mice (10/group) were fed *B. longum* AH1205 or placebo for three weeks. Following probiotic/placebo consumption, $CD4^+$ $CD25^+$ T-regulatory cells were isolated and their in vitro suppressive activity was determined by measuring proliferation of anti-CD3/CD28 stimulated CFSE-labeled $CD4^+$ responder T cells using flow cytometry. $CD4^+$ responder T cells were co-incubated with $CD4^+CD25^-$ T cells as a control. The percentage of $CD4^{+CD}25^+$ cells (regulatory T cells) in murine splenocytes that were also FoxP3 positive was determined in the spleens of probiotic or placebo-fed mice.

Figure 7:
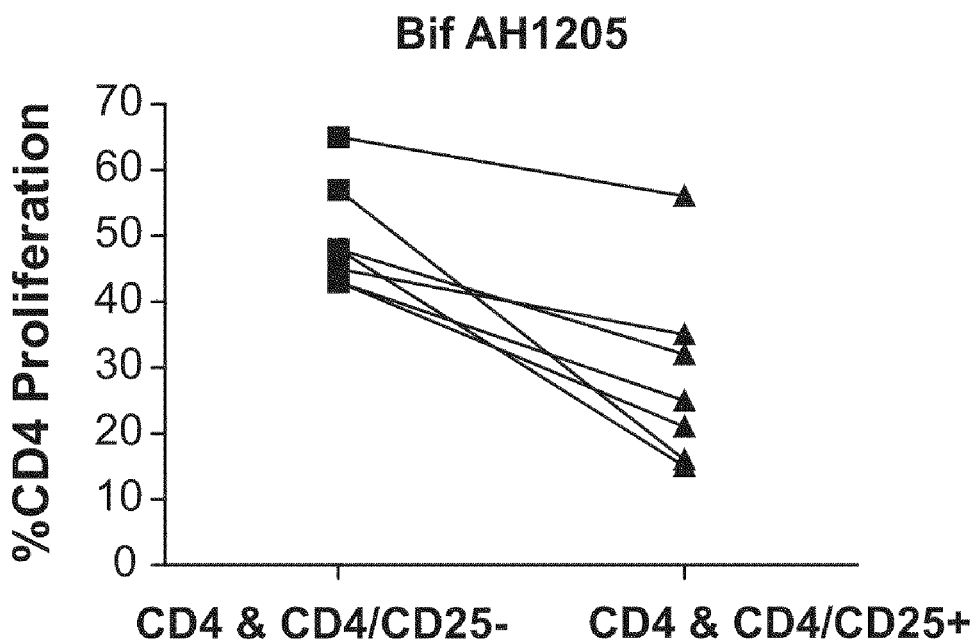
FIG. 7 is a graph illustrating that CD4$^+$ CD25$^+$ cells from AH1205-fed mice significantly reduced responder CD4$^+$T cell proliferation (n=7)

The percentage of $CD4^+$ cells that proliferated when co-incubated with $CD4^+CD25^+$ cells from the probiotic/placebo fed mice was compared to the percentage of $CD4^+$ cells that proliferated when co-incubated with $CD4^+CD25^-$ cells from the same trial mouse. In each case, T cell proliferation was less in cultures containing $CD4^+CD25^+$ cells compared in cultures containing $CD4^+$ cells alone and depleted of the $CD25^+$ cells (FIG. 7).

Figure 8:
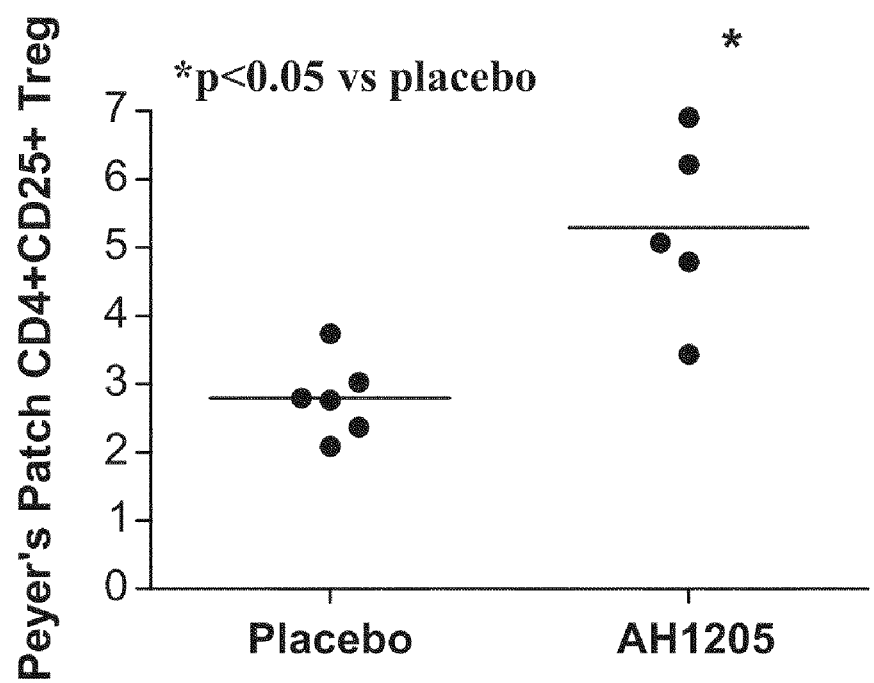
FIG. 8 is a graph showing the percentage of Payer's patch cells in the CD4$^+$ population that are also CD25$^+$, as assessed by flow cytometry.

The percentage of cells in the $CD4^+$ population that were also $CD25^+$ was determined (FIG. 8). The *B. longum* AH1205-fed group had significantly more $CD4^+$T cells that were $CD25^+$ (i.e. T-regulatory cells) than their placebo-fed counterparts. This suggests that the percentage of T-regulatory cells within the $CD4^+$ population was increased significantly by feeding with AH1205. This result indicates that AH1205 administration may reduce or prevent inflammation within a human.

The number of $CD4^+CD25^+FoxP3^+$ cells in the whole splenocyte populations of probiotic or placebo-fed mice was also determined. The number of $CD4^+CD25^+$T-Regulatory cells expressing FoxP3 was unchanged in the spleens of probiotic fed mice relative to placebo or unfed mice.

EXAMPLE 5

Germ-free mice were purchased at 6 weeks of age and maintained in the germ-free unit at the biological services unit in UCC. Animals consumed the probiotic strain *B. longum* AH1205 for 9 days or remained germ-free (control). Induction of T regulatory cells was assessed by flow cytometry and cytokine levels were quantified by CBA.

AH1205 transit was assessed by measuring *bifidobacterial* counts on selective agar over the course of the study. AH1205 did not transit the gut of germ-free mice in measurable numbers even though approximately $1\times10^9$ organisms were administered daily. This result suggests that additional microbial or host factors are required for *bifidobacterial* survival within the gut.

While AH1205 did not transit the gut in detectable numbers, the bacteria did interact with the host immune system. The numbers of $CD4^+$ $CD25^+FoxP3^+$ cells in the mesenteric lymph node and spleen of AH1205-fed germ-free animals were significantly increased following 9 days of feeding (FIG. 9). Total CD3/CD4 or CD3/CD8 counts remained unaltered.

Figure 11:
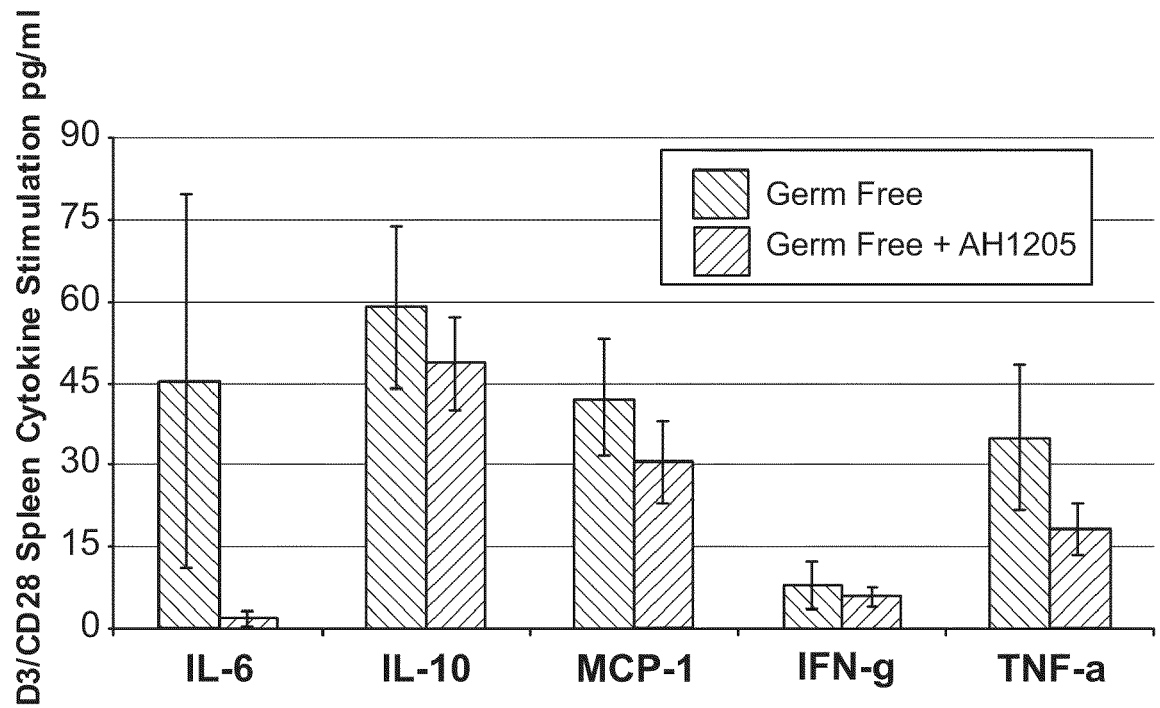
FIG. 11 is a graph showing that the level of cytokines IL-6 and TNF-α secreted by CD3/CD28 stimulated splenocyte cultures was reduced when germ-free mice consumed B. longum AH1205. Results are expressed as the mean per group±SEM (n=4/group)

Isolated MLNC and splenocytes were stimulated in vitro with anti-CD3/CD28 antibodies or LPS or remained un-stimulated as negative controls. MLNC secretion of IL-6 and IFN-γ, following CD3/CD28 stimulation, was substantially decreased in culture supernatants while MCP-1 levels were significantly suppressed when mice were pre-fed AH1205 (FIG. 10). IL-10 levels remained similar between the groups. Splenocyte release of IL-6 and TNF-α was substantially, but not significantly, decreased when pre-fed AH1205 (FIG. 11). No significant differences were noted for the unstimulated or LPS stimulated cultures but overall less pro-inflammatory cytokine production was observed from the *B. longum* AH1205-fed animals. Again, this result indicates that AH1205 administration may reduce or prevent inflammation within a human.

EXAMPLE 6

Figure 12:
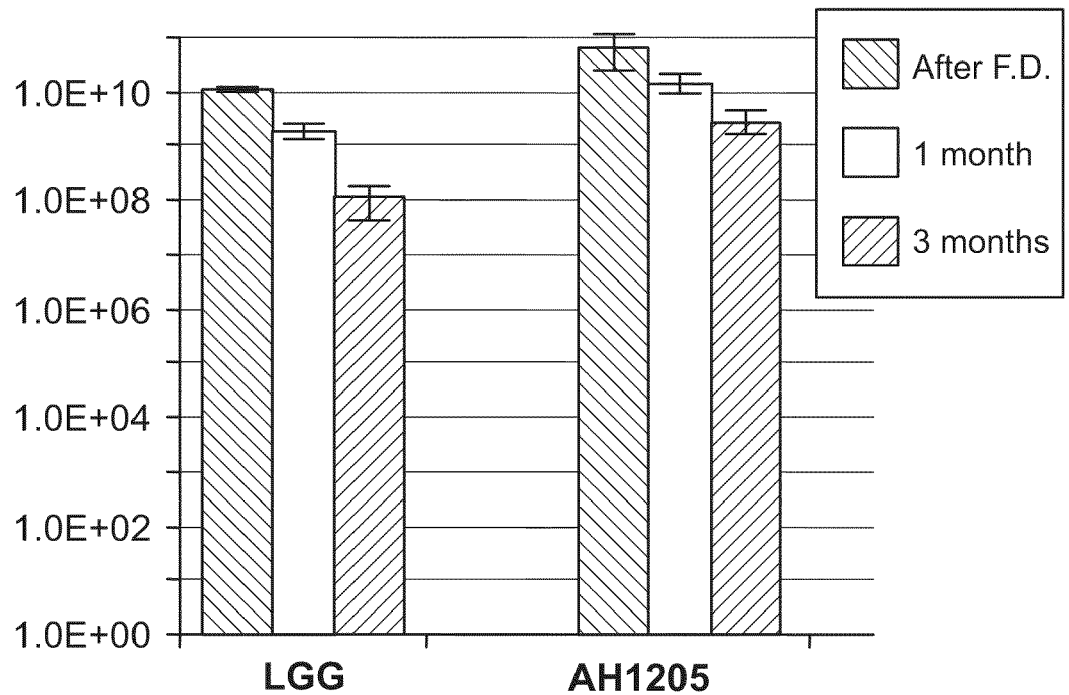
FIG. 12 is a graph illustrating the stability of B. longum AH1205 over 3 months as compared to Lactobacillus rhamnosus GG (LGG).

This example illustrates the stability of *B. longum* AH1205. The stability of AH1205 varied over 3 months at 30° C. (FIG. 12). LGG was a poor performer over the test period with a 2 log drop over the 3 month period whereas strain AH 1205 declined in viability by up to approximately 1 log over the same test period.

All references cited in this specification, including without limitation, all papers, publications, patents, patent applications, presentations, texts, reports, manuscripts, brochures, books, internet postings, journal articles, and periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A nutritionally complete infant formula comprising a protein source providing from about 1 to about 5 g/100 kcal of protein, a fat or lipid source providing from about 3 to about 7 g/100 kcal of fat or lipid, a carbohydrate source providing from about 8 to about 12 g/100 kcal of carbohydrates, a source of long chain polyunsaturated fatty acids comprising docosahexaenoic acid, and *B. longum* AH1205.

2. The infant formula of claim 1, wherein the infant formula comprises *B. longum* AH1205 in the range of about $1 \times 10^4$ cfu to about $1 \times 10^{10}$ cfu per gram infant formula.

3. The infant formula of claim 1, wherein the infant formula comprises *B. longum* AH1205 in the range of about $1 \times 10^6$ cfu to about $1 \times 10^9$ cfu per gram infant formula.

4. The infant formula of claim 1, wherein the infant formula comprises at least $1 \times 10^6$ cfu *B. longum* AH1205 per gram infant formula.

5. The infant formula of claim 1, wherein the *B. longum* AH1205 is viable.

6. The infant formula of claim 1, wherein the *B. longum* AH1205 is non-viable.

7. The infant formula of claim 1, further comprising an additional probiotic.

8. The infant formula of claim 7, wherein the additional probiotic comprises *Lactobacillus rhamnosus* GG.

9. The infant formula of claim 1, further comprising a prebiotic.

10. The infant formula of claim 9, wherein the prebiotic is selected from the group consisting of oligosaccharides, polysaccharides, and prebiotics that contain fructose, xylose, soya, galactose, glucose or mannose.

11. The infant formula of claim 9, wherein the prebiotic is selected from the group consisting of lactulose, gluco-oligosaccharide, inulin, polydextrose, galacto-oligosaccharide, fructo-oligosaccharide, isomalto-oligosaccharide, soybean oligosaccharides, lactosucrose, xylo-oligosaccharide, and gentio-oligosaccharides.

12. The infant formula of claim 1, further comprising arachidonic acid.

13. The infant formula of claim 12, wherein the ratio of arachidonic acid:docosahexaenoic acid by weight is from about 1:3 to about 9:1.

14. The infant formula of claim 1, wherein the infant formula comprises a form selected from the group consisting of a powder, a liquid, and a ready-to-use formulation.

15. The infant formula of claim 9, wherein the prebiotic comprises polydextrose and galacto-oligosaccharide.

* * * * *